United States Patent [19]

Köster et al.

[11] 4,172,195

[45] Oct. 23, 1979

[54] PROCESS FOR THE SEPARATION AND PURIFICATION OF OLIGO AND POLYHYDROXY COMPOUNDS AND BORATE ESTERS THEREOF

[75] Inventors: Roland Köster; Wilhelm V. Dahlhoff, both of Mülheim, Fed. Rep. of Germany

[73] Assignee: Studiengesellschaft Kohle mbH, Kaiser-Wilhelm-Platz, Fed. Rep. of Germany

[21] Appl. No.: 783,351

[22] Filed: Mar. 23, 1977

[30] Foreign Application Priority Data

Mar. 25, 1976 [AT] Austria .................................. 2208/76

[51] Int. Cl.² ............................................. C07H 23/00
[52] U.S. Cl. ................................... 536/4; 260/462 R; 568/854; 536/32; 536/48; 536/101; 536/115; 536/121
[58] Field of Search ..................... 536/121, 115, 4, 58, 536/101, 121, 32, 48; 260/462 R, 635 E

[56] References Cited

U.S. PATENT DOCUMENTS

| | | | |
|---|---|---|---|
| 3,067,192 | 12/1962 | Emrick et al. | 536/115 |
| 3,222,379 | 12/1965 | Farthouat | 536/115 |
| 3,231,561 | 1/1966 | Brunelle et al. | 536/115 |
| 3,853,941 | 12/1974 | Hough et al. | 260/462 R |
| 3,891,621 | 6/1975 | Arthur, Jr. et al. | 536/121 |
| 3,923,781 | 12/1975 | Rogers | 536/121 |

*Primary Examiner*—Johnnie R. Brown
*Attorney, Agent, or Firm*—Sprung, Felfe, Horn, Lynch & Kramer

[57] ABSTRACT

A process for the separation and/or purification of oligo- and polyhydroxy compounds by introducing and subsequently eliminating protective groups, wherein oligo- and polyhydroxy compounds are reacted with bis(ethyl-pivaloyloxy)-diboroxane or ethylboroxine, optionally in inert solvents, the resulting O-ethylboranodiyl derivatives of the hydroxy compounds are separated off and the O-ethylboranodiyl protective groups are eliminated by alcoholic compounds, for example methanol or glycol.

36 Claims, No Drawings

PROCESS FOR THE SEPARATION AND PURIFICATION OF OLIGO AND POLYHYDROXY COMPOUNDS AND BORATE ESTERS THEREOF

Oligo and polyhydroxy compounds are becoming increasingly more important as starting and intermediate products for pharmaceuticals or as backbone compounds for environmentally acceptable plastics. Accordingly, equal importance is attached to purification and separation processes for processing the hydroxy-containing compounds. For example, the separation of glucose and xylose from hardwood pulp, which hitherto has never been chemically exploited to any significant extent, or the separation of the starch constituents is currently being attempted on a commercial scale by means of new processes. Processes such as these frequently necessitate the formation of derivatives in as selective a manner as possible. Accordingly, protective groups capable of being introduced and eliminated again under the mildest possible conditions are required for the hydroxyl functions. The basic structure of the hydroxy compounds should remain in tact. Although there has long been a large number of so-called protective groups which satisfy many of the requirements made of them, they frequently fail to live up to expectations. Thus, the widely used isopropylidene group for example can only be removed again by treatment with an acid. At the same time, however, O-acyl radicals, for example on the glycoside C-atom, are often very easily and completely split off again.

It has now been found that the bifunctional O-ethylboranodiyl group is capable of meeting the abovementioned requirements for a protective function for polyhydroxy compounds more effectively than the bifunctional radicals hitherto used such as, for example, O-isopropylidene and O-benzylidene radicals. In addition, the O-ethylboranodiyl groups also afford possibilities for the regio- and stereo-selective conversions of certain hydroxyl groups of oligo and polyhydroxy compounds.

According to the invention, the O-ethylboranodiyl groups can be introduced into the hydroxy compounds, for instance by means of bis-(ethylpivaloyloxy)-diboroxane (BEPDIB) the anhydride of ethylpivaloyloxy boric acid or ethylboroxin:

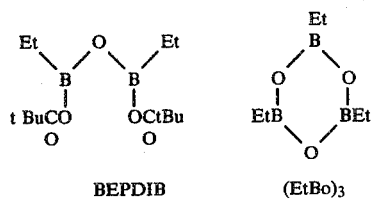

BEPDIB          (EtBo)$_3$

Isomer-free derivatives of the hydroxy compounds with the O-ethylboranodiyl groups attached to the molecule through two oxygen atoms are generally obtained in a substantially quantitative yield in accordance with the following equation:

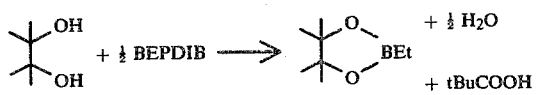

-continued

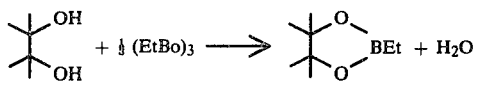

Depending upon the number and spatial arrangement of the hydroxy groups present, it is possible in accordance with the invention to introduce two or even more O-ethylboranodiyl radicals into one molecule. In addition, however, the introduction of intermolecularly bound O-ethylboranodiyl groups is also possible.

Suitable hydroxy compounds are for example 1,2-alkane diols, 1,3-alkane diols, 1,2,4-alkane triols, 1,2,3,4-alkane tetraols, alkane pentaols, alkane hexaols and other alkane polyols. Other suitable compounds are aldo- and keto-tri- to -heptaoses and also di-, tri- and other oligosaccharides. Desoxy sugars and also sugar carboxylic acids and their anhydrides may also be used in accordance with the invention. Any polymers containing hydroxy groups such as, for example, starch or cellulose may also be used.

The derivatives of the hydroxy compounds exclusively containing intramolecular O-ethylboranodiyl radicals are always obtained when 0.5 mole of BEPDIB or ⅓ mol ethylboroxin is used for 2 sterically attachable hydroxyl groups and quantitatively reacted. When BEPDIB or ethylboroxin is used in excess, intermolecular O-ethylboranodiyl derivatives are obtained from all compounds with an uneven number of hydroxyl groups. In addition, the hydroxy compounds with an uneven number of OH-groups also form O-ethylboranodiyl derivatives with intermolecular linkage where they cannot be intramolecularly attached for steric reasons.

Despite the numerous possible isomerisms, the intramolecular O-ethylboranodiyl derivatives of the monosaccharides are completely homogeneous and can generally be distilled in vacuo without decomposition. The number and stereochemistry of the free hydroxy groups is critical to the number of intramolecularly introducible O-ethylboranodiyl groups. For four hydroxy groups in one compound, 1 mole of BEPDIB or ⅔ mol ethylboroxin is required when 2 O boranodiyl groups can be intramolecularly introduced by virtue of the steric conditions. Aldo- and keto-pentoses contain for example four and aldo- and keto-hexoses for example five hydroxy groups capable of substitution by an O-ethyl borane radical. Accordingly, the bis-O-ethylboranodiyl derivatives of the aldo- and keto-pentoses for example have the general formula $C_5H_6O_5(BEt)_2$. By contrast, the corresponding derivatives of the aldo- and keto-hexoses with the general formula $C_6H_8O_6(BEt)_2$ contain one free hydroxyl group. According to the invention, glucose, mannose or fructose can be converted into homogeneous bis-O-ethylboranodiyl derivatives as easily and as quantitatively as, for example, ribose, arabinose or xylose. In every case, only one anomer or a ring isomer is formed in a substantially quantitative yield.

The process according to the invention is extremely easy to carry out. The undiluted mixture of oligo or polyhydroxy compound and BEPDIB or ethylboroxin is heated for example to approximately 80° C. Then O-ethylboranodiyl radicals can be introduced at temperatures of from about −10° C. to about +150° without the occurrence of any secondary reactions. Water and pivalic acid or only water are eliminated. Pyridine for example is advantageously used as diluent, although other solvents are also suitable. Thus, aliphatic hydrocarbons such as pentane, hexane, heptane, iso-octane, decane or aromatic hydrocarbons such as benzene, toluene, xylene and also cycloaliphatic hydrocarbons and cyclo-olefins such as cyclo-octene, cyclohexene, cyclo-octadiene, decalin or methyl naphthalene may be used as solvents. Chlorinated hydrocarbons, such as chlorobenzene, chloroform or carbon tetrachloride and also ethers such as diethyl ether, ethylbutyl ether, dibutylether or dioxane or tetrahydrofuran may also be used. The intramolecular O-ethylboranodiylisation of the polyhydroxy compounds takes place quickly and quantitatively at room temperature, for example in pyridine. A maximum of 0.5 mole of BEPDIB or ⅓ mole ethylboroxin is used for 2 hydroxy groups. Any increase in the quantity of BEPDIB or in the quantity of ethylboroxin used produces the intermolecular O-ethylboranodiylisations referred to above. These reactions are desirable for certain separations of substances.

Formation of the saccharide derivatives is highly productive. The pure O-ethylboranodiyl derivatives of the monosaccharides obtainable in accordance with the invention are soluble in hydrocarbons. In addition, intramolecular O-ethylboranodiyl derivatives of the monosaccharides can be distilled in vacuo without decomposition.

The compounds obtainable in accordance with the invention show no changes after storage in dry air at room temperature, even for several days. However, the O-ethylboranodiyl derivatives are capable of reacting with proton-containing substances. The reaction of BEPDIB or ethylboroxin with the hydroxy compounds should be carried out as far as possible in the absence of water, alcohols and foreign hydroxy-containing compounds because otherwise reagent is consumed and the O-ethylboranodiylisation is only incomplete.

Providing certain conditions are maintained, the O-ethylboranodiyl derivatives can be partially or even selectively de-borylated with certain protolysis agents, such as alcoholic compounds, preferably methanol or glycol. This provides for new specific O-derivative formations for oligohydroxy compounds. Complete deborylation leads back to the original saccharides or, after previous O-derivative formation, to their derivatives. Highly pure compounds are generally obtained.

Accordingly, the process according to the invention is suitable for the purification of polyhydroxy compounds. Above all, saccharides or their derivatives can be obtained in high yields and purity. This can be achieved for example by distillation. In many cases, an O-ethylboranodiyl derivative can be distilled off in vacuo without decomposing from involatile derivatives or impurities.

Monosaccharides can thus be readily separated from the disaccharides. The separations are complete without any loss of the substances used. The process according to the invention is also suitable for the separation of various hydroxy compounds. The O-ethylboranodiyl derivatives of, for example, the pentitols and hexitols or those of the pentoses and hexoses can be separated from one another. This is because the alternate intra- and inter-molecular introduction of the O-ethylboranodiyl radicals allows the conversion of two components into a distillable compound and a non-distillable compound.

In addition, the O-ethylboranodiyl derivatives are suitable for the regioselective O-derivative formation of alkane oligo or polyols and of saccharides or saccharide derivatives.

The O-ethylboranodiyl radicals introducible in accordance with the invention are distinctly superior in a few important features to the usual bifunctional protective groups such as, for example, the O-isopropylidene or O-benzylidene radicals. This is because the O-ethylboranodiyl radicals can be introduced into the hydroxy compounds not only extremely carefully, but also in particularly good yields. In addition, the process according to the invention directly gives particularly pure products. Also, relatively little time is required for carrying out the process. In particular, the O-ethylboranodiyl groups can be eliminated again under comparatively mild chemical and thermal conditions. Accordingly, the reaction according to the invention affords good possibilities for the regioselective O-derivative formation of alkane polyols, saccharides and their derivatives. This is illustrated by the four Comparison Examples in Table 1.

TABLE 1

O-derivative formation of monosaccharides with and without O-ethylboranodiyl derivatives as intermediates

| Starting compound | End product | % yield A | % yield B | Literature reference |
|---|---|---|---|---|
| D-fructose | 1-O-benzoyl-D-fructopyranose | 61 | 13 | (a) |
| Methyl-β-L-arabino-pyranoside | 2-O-benzoylmethyl-β-L-arabino-pyranoside | 75 | 44 | (b) |
| D-glucose | 6-O-acetyl-D-glucopyranose | 79 | 25 | (c) |
| L-sorbose | 1-O-benzoyl-L-sorbose | 69 | 37 | (d) |

A = with the process according to the invention
B = with hitherto used protective groups Some O-derivatives of saccharides which could not be obtained with conventional processes can readily be obtained by the process according to the invention. The 1-O-benzoyl-D-mannofuranose (K. Freudenberg & A. Wolf, Ber. 300 (1925)), 1-O-acetyl-2-desoxy-D-ribopyranose and 1,5-di-O-acetyl-L-rhamnofuranose (K. Freudenberg & A. Wolf, Ber. 59, 836 (1926)), which cannot be obtained by means of the known protective groups, can be obtained in high yields and in pure form by way of O-ethylboranodiyl derivatives.

The O-ethylboranodiyl derivatives obtained by the reaction of polyhydroxy compounds with bis-(ethylpivaloyl)-diboroxane or ethylboroxin are new compounds. Some representatives of this group of compounds, whose production is described in the following Examples, are summarised below. Their specific characterisation is not only by the optical rotation value and the melting point, but also and above all by the $^1$H-, $^{11}$B- and $^{13}$C-NMR-spectra:

(I) 1,2:3,4-bis-O-ethylboranodiyl-α-D-ribopyranose (bp. 78° C./10$^{-3}$ Torr, $[\alpha]_D^{20}$ 9.9 (c=2, CCl$_4$), Observed: B=9.50%, B$_C$=3.27%)

(II) 1,2:3,4-bis-O-ethylboranodiyl-β-L-arabinopyranose (bp. 68°–69° C./10$^{-3}$ Torr, $[\alpha]_D^{20}$ 10.9 (c=3.8, CCl$_4$), Observed: B=9.60%, B$_C$=3.40%)

(III) 1,2:3,5-bis-O-ethylboranidyl-α-D-xylofuranose (bp. 74° C./10$^{-3}$ Torr, $[\alpha]_D^{20}$ 33.4 (c=2, CCl$_4$) Observed: B 9.50%, B$_C$=3.10%)

(IV) 1,2:3,5-bis-O-ethylboranodiyl-β-L-rhamnopyranose (bp. 77°–78° C./10$^{-3}$ Torr, $[\alpha]_D^{21}$ −10.2 (c=2.9, CCl$_4$), Observed: B=9.05%, B$_C$=2.97%)

(V) 3,4-O-ethylboranodiyl-2-desoxy-β-D-ribopyranose with a free OH-group in the 1-position (bp. 95°-98° C./10⁻³ Torr, mp. 88° C., [α]$_D^{20}$ −55.8 (c=0.7, DMSO), Observed: B=6.20%, B$_C$=1.96%, H⊕=0.64%)

(VI) 2,3:5,6-bis-O-ethylboranodiyl-α-D-mannofuranose with a free OH-group in the 1-position (bp. 126° C./10⁻³ Torr, [α]$_D^{20}$ +19.2 (c=1.7, DMSO), Observed: B=8.43%, B$_C$=2.79%, H⊕=0.41%)

(VII) 1,2:3,5-bis-O-ethylboranodiyl-α-D-glucofuranose with a free OH-group in the 6-position (bp. 120° C./10⁻³ Torr, [α]$_D^{20}$ +50.5 (c=4.6, DMSO), Observed: B=8.38%, B$_C$=2.46%, H⊕=0.4%)

(VIII) 1,2:3,4-bis-O-ethylboranodiyl-α-D-galactopyranose with a free OH-group in the 6-position (bp. 119° C./10⁻³ Torr, [α]$_D^{20}$ 13.1 (c=1.1, DMSO) Observed: B=8.5%, B$_C$=2.90%, H⊕=0.45%)

(IX) 2,3:4,6-bis-O-ethylboranodiyl-α-methyl-D-mannopyranoside (bp. 100° C./10⁻³ Torr, [α]$_D^{20}$ −9.9 (c=7, hexane), Observed: B=8.2%, B$_C$=2.8%)

(X) 4,6-O-ethylboranodiyl-α-methyl-D-glucopyranoside with free OH-groups in the 2- and 3-position (bp. 140° C./10⁻³ Torr, [α]$_D^{20}$ 79.9 (c=1.1, dioxane) Observed: B=4.69%, B$_C$=1.56%, H⊕=0.86%)

(XI) 2,4-O-ethylboranodiyl-β-methyl-D-xylopyranoside with a free OH-group in the 3-position (bp. 58° C./10⁻³ Torr, [α]$_D^{20}$ −113 (c=4.8, CCl₄) Observed: B=5.40%, B$_C$=1.77%, H⊕=0.5%)

(XII) 2,3:4,5-bis-O-ethylboranodiyl-β-D-fructopyranose with a free OH-group in the 1-position (bp. 99° C./10⁻³ Torr, [α]$_D^{20}$ −52 (c=3.7, DMSO), Observed: B=8.4%, H⊕=0.4%)

(XIII) 2,3:4,6-bis-O-ethylboranodiyl-α-L-sorbofuranose with a free OH-group in the 1-position (bp. 120° C./10⁻³ Torr, [α]$_D^{20}$ −36.8 (c=6.1, DMSO), Observed: B=8.4%, B$_C$=2.75%, H⊕=0.39%)

(XIV) 1,2:3,4-bis-O-ethylboranodiyl-D-tagatofuranose with a free OH-group in the 5-position (bp. 98° C./10⁻³ Torr)

(XV) 3,4-O-ethylboranodiyl-β-methyl-L-arabinopyranoside with a free OH-group in the 2-position (bp. 75° C./10⁻³ Torr, [α]$_D^{20}$ 26.8 (c=1, DMSO), Observed: H⊕=0.49%)

(XVI) 2,3-O-ethylboranodiyl-β-D-ribopyranoside with free OH-groups in the 1- and 4-position (bp. 130° C./10⁻³ Torr, [α]$_D^{20}$ −38.8 (c=1.9, DMSO)

(XVII) 2,3-O-ethylboranodiyl-α-rhamnofuranose with free OH-groups in the 1- and 5-position ([α]$_D^{20}$ 6.2 (c=3.3, DMSO))

(XVIII) 2,3-O-ethylboranodiyl-D-ribopentono-1,4-lactone with a free OH-group in the 5-position (bp. 157° C./10⁻³ Torr, [α]$_D^{20}$ −95 (c=4.2, DMSO) Observed: B=5.75%, B$_C$=1.86%)

(XIX) 1,2-O-ethylboranodiyl-D-glucurono-3,6-lactone with a free OH-group in the 5-position (mp. 48° C., [α]$_D^{20}$ 77.8 (c=2.3, CCl₄), Observed: B$_C$=1.6%)

(XX) 4,6-O-ethylboranodiyl-N-acetyl-D-glucosamine with free OH-groups in the 1- and 3-position (Observed: B=4.42%, B$_C$=1.35%)

The intermolecular O-ethylboranodiyl derivatives obtainable in accordance with the invention consist for example of two saccharide molecules. They are viscous liquids. The so-called hexose dimers with the general formula (C₆H₇O₆)₂(BEt)₅ are formed for example from glucose in accordance with the following equation:

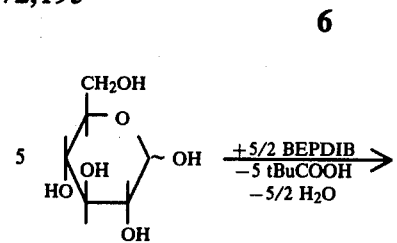

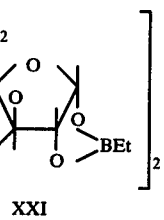

XXI

Compound XXI from glucose, like compound XXII from mannose, is a colourless, viscous non-distillable liquid.

The intramolecular and intermolecular O-ethylboranodiyl derivatives of the alkane polyols and those of the mono-, di- and tri-saccharides are equally well soluble in aliphatic or aromatic hydrocarbons. The intramolecular O-ethylboranodiyl derivatives of the alkane oligools, such as for example those of the hexitols and those of the monosaccharides, are liquids which can be distilled in vacuo without any decomposition. By contrast, the intramolecular O-ethylboranodiyl derivatives of the disaccharides cannot be distilled. This is also the case with the derivatives of the monosaccharides with an intermolecular O-ethylboranodiyl group.

DESCRIPTION OF THE EXPERIMENTS

All the experiments are carried out in the absence of moisture and air. They are advantageously carried out under the protection of an inert gas such as, for example, pure nitrogen or argon.

EXAMPLE 1

1,2:3,4-bis-O-ethylboranodiyl-β-L-arabinopyranose (II)

A solution of 22.4 g (75.3 mmole) of BEPDIB in 20 ml of benzene is added at room temperature to a stirred suspension of 7.5 g (50 mmole) of L-arabinose in 20 ml of benzene. After stirring for 30 minutes, 0.5 g of unchanged L-arabinose is filtered off. After concentration in vacuo, distillation gives 9.5 g (90%) of 99.3% pure (GC) II of bp. 68°-69° C./10⁻³ Torr; [α]$_D^{20}$ +10.9 (c=3.8, CCl₄); 0.9 g of dark brown residue. ¹¹B-NMR (2,2-dimethylbutane): δ=35.4 ppm (Hwb=900 c/s); observed 9.6% B, calculated 9.57% B.

EXAMPLE 2

3,4-O-ethylboranodiyl-2-desoxy-D-ribose (V)

A solution of 5.5 g (18.5 mmole) of BEPDIB in 10 ml of benzene is added dropwise over a period of 15 minutes at room temperature to a stirred solution of 5 g (37.3 mmole) of 2-desoxy-D-ribose in 20 ml of pyridine. The mixture is concentrated in vacuo. Subsequent distillation gives 6.2 g (97%) of crystalline V of bp. 95°-98° C./10⁻³ Torr and mp. 88° C.; [α]$_D^{20}$ −55.8 (c=0.7, DMSO).− ¹¹B-NMR (acetonitrile): 32.9 ppm (Hwb=220 c/s).- Observed: B 6.2%, calculated: B 6.29%.

Other polyhydroxy compounds according to Table 2 are similarly reacted:

Table 2

O-boranodiylisation of aldopentoses, desoxy-pentoses and hexoses with BEPDIB

| Example | Pentose Name | Weighed quantity g | mmole | BEPDIB g | mmole | Distillation product No. | g (%)(x) | b.p. °C./10⁻³ Torr (m.p.) | % B (% BC)(xx) calc. | observ. | $[\alpha]_D^{20}$ (c, CCl₄) |
|---|---|---|---|---|---|---|---|---|---|---|---|
| 2 | 2-desoxy-D-ribose | 5 | 37.3 | 5.5 | 18.5 | V | 6.2 (97) | 95–98 (88) | | | −55.8 (0.7, DMSO) |
| 3 | L-arabinose | 7.5 | 50 | 22.4 | 75.3 | II | 9.5 | 68–69 | 9.57 (3.19) | 9.60 (3.40) | +10.9 (3.8) |
| 4 | D-xylose | 4.2 | 28 | 18.3 | 61.4 | III | 5.8 (92) | 74 | 9.57 | 9.50 | 33.4 (2) |
| | | 5 | 33.3 | 9.9 | 33.2 | III | 5.8 (99) | | (3.19) | (3.10) | |
| 5 | D-ribose | 4.5 | 30 | 19.3 | 64.8 | I | 6.2 (92) | 78 | 9.57 | 9.50 | 9.9 (2) |
| | | 5.3 | 35.3 | 10.6 | 35.6 | | 7.2 (90) | 78 | (3.19) | (3.27) | |
| | | 5.1 | 34 | 10.1 | 33.9 | | 6.2 (92) | 78 | | | |
| 6 | L-rhamnose =6-desoxy-L-mannose | 4.1 | 25 | 7.4 | 24.8 | IV | 5.7 (96) | 77–78 | 9.01 (3.00) | 9.05 (2.97) | −10.2 (2.9) |

(x)based on conversion
(xx)Liebigs Ann. Chem. 704, 70 (1967)

Other polyhydroxy compounds according to Table 3 are similarly reacted.

TABLE 3

O-ethylboranodiylisation of aldo- and ketohexoses with BEPDIB

| Example | Hexose Name | g | mmole | BEPDIB g | mmole | Distillation Product No. | g (%) | % B (% B_C) calc. | observ. | $[\alpha]_D^{20}$ (c, DMSO) | b.p. °C./10⁻³Torr |
|---|---|---|---|---|---|---|---|---|---|---|---|
| 8 | D-fructose | 5 | 27.8 | 8.4 | 28.2 | XII | 6.8 (96) | 8.45 (2.82) | 8.40 (2.78) | −52 (3.7) | 99 |
| 9 | D-glucose | 10 | 55.5 | 16.5 | 55.4 | VII | 13.3 (94) | 8.45 (2.82) | 8.38 (2.46) | 50.5 (4.6) | 120 |
| 7 | D-mannose | 5 | 27.8 | 8.3 | 27.8 | VI | 8.6 (96) | 8.45 (2.82) | 8.43 (2.79) | 19.2 (1.7) | 126 |
| 10 | D-galactose | 5 | 27.8 | 8.4 | 28.2 | VIII | 7 (99) | 8.45 (2.82) | 8.50 (2.90) | 13.1 (1.1) | 119 |
| 11 | L-sorbose | 5 | 27.8 | 8.4 | 28.2 | XIII | 6.8 (96) | 8.45 (2.82) | | −36.8 (6.1) | 120 |
| 12 | D-tagatose | 2 | 11.1 | 3.3 | 11.1 | XIV | 2.7 (95) | 8.45 (2.82) | | | 98 |

EXAMPLE 7

2,3:5,6-bis-O-ethylboranodiyl-α-D-mannofuranose (VI)

8.3 g (27.8 mmole) of BEPDIB in 20 ml of benzene are added dropwise over a period of 10 minutes at room temperature to 5 g (27.8 mmole) of D-mannose in 20 ml of pyridine. Removal of the readily of the readily volatile constituents leaves 6.8 g (96%) of a colourless liquid (VI) of bp. 126° C./10⁻³ Torr; $[\alpha]_D^{20}$ +19.2 (c=1.7, DMSO). Observed: B 8.43% <calculated: B 8.45%>

EXAMPLE 8

2,3:4,5-bis-O-ethylboranodiyl-β-D-fructopyranose (XII)

A solution of 8.4 g (27.8 mmole) of BEPDIB in 20 ml of benzene is added dropwise over a period of 1 hour at room temperature to a stirred suspension of 5 g (27.8 mmole) of fructose in 20 ml of pyridine. Removal of the readily volatile constituents in vacuo (10⁻¹ to 10⁻³ Torr) leaves 6.8 g (96%) of a colourless liquid (XII) of bp. 98°–99° C./10⁻³ Torr; $[\alpha]_D^{20}$ −52 (c=3.7, DMSO); 0.3 g of brown residue. Observed: B 8.4%, H⊕ 0.42% <Calculated: B 8.45%, H⊕ 0.4%>

EXAMPLE 13

O-Ethylboranodiylisation of saccharides with BEPDIB in the absence of solvent XXI from D-glucose A mixture of 3.4 g (18.9 mmole) of D-glucose and 18.5 g (62 mmole) of BEPDIB (cf. the reaction equation above, immediately following the listing of compounds I–XX); is heated with stirring for 30 minutes to 80° C. Removal of the readily volatile constituents by distillation in vacuo leaves 5 g (96.5%) of viscous product XXI, which is 6,6'-O-ethylboranodiyl-bis-(1,2,:3,5-di-O-ethylboranodiyl-α-D-glucofuranose);

¹H-NMR (60 Mc/s, CCl₄): τ=5.85 and 9.13 ppm in the observed ratio 12.4:26.6; calc. 14:25.

C₂₂H₃₉O₁₂B₅ (549.6) Observed: B 9.59, Calculated B 9.84

EXAMPLE 14

XXII from D-mannose 5.4 g (99%) of viscous product XXII are obtained from 3.6 g (20 mmole) of mannose and 18.2 g (61 mmole) of BEPDIB (cf. the reaction equation above, immediately following the listing of compounds I–XX);

Other polyhydroxy compounds according to Tables 4, 5 and 6 are similarly reacted.

Table 4

O-ethylboranodiylisation of methyl glycosides with BEPDIB

| Example | Methyl glycoside Name | g | mmole | BEPDIB g | mmole | Distillation product No. | g (%) | b.p. (m.p.) °C./10⁻³ Torr | % B (% B_C) calc. | observ. | $[\alpha]_D^{20}$ (c, LM) |
|---|---|---|---|---|---|---|---|---|---|---|---|
| 15 | β-methyl-D-xylopyranoside | 5 | 30.5 | 4.6 | 15.4 | XI | 5.1 (83) | 58 | 5.35 (1.78) | 5.40 (1.77) | −11 (4.8 CCl₄) |
| 16 | β-methyl-l-arabinose pyranoside | 2 | 12.2 | 1.8 | 6 | XV | 1.9 (91) | 75 | | | 26.8 (1,DMSO) |
| 17 | α-methyl-D-glucopyranoside | 5 | 25.8 | 3.9 | 13.1 | X | 5.9 (99) | 140 (47) | 4.66 (1.55) | 4.69 (1.56) | 78 (3.9, dioxane) |
| 18 | α-methyl-D-mannopyranoside | 5.1 | 26.3 | 7.9 | 26.5 | IX | 7.1 (100) | 100 (86) | 8.01 (2.67) | 8.23 (2.80) | −9.9 (7, hexane) |

Table 5

O-ethylboranodiylisation of sugar lactones with BEPDIB

| Example | Lactone Name | g | mmole | BEPDIB g | mmole | Distillation product No. | g (%) | b.p. (m.p.) °C./10⁻³ Torr | % B (% B_C) calc. | observ. | $[\alpha]_D^{20}$ (c, LM) |
|---|---|---|---|---|---|---|---|---|---|---|---|
| 19 | D-ribopent-ono-1,4-lactone | 7.2 | 48.6 | 7.2 | 24.3 | XVIII | 8.8 (97) | 157 | 5.81 (1.94) | 5.75 (1.86) | −95 (4.2, DMSO) |
| 20 | D-glucurono-3,6-lactone | 5.3 | 30.1 | 4.5 | 15 | XIX | 6.4 (99) | (48) | | | +77 (2.3; CCl₄) |

Table 6

O-ethylboranodiylisation of polyalcohols with BEPDIB

| Example | Polyalcohol Name | g | mmole | BEPDIB g | mmole | Product g (%) | b.p. (°C.) | %B (%B_C) calc. | observ. |
|---|---|---|---|---|---|---|---|---|---|
| 21 | ethane-1,2-diol | 1.86 | 30 | 17.9 | 60 | 2.9 (97) | 105 | 10.82 (3.61) | 10.76 (3.57) |
| 22 | butane-1,2,4-triol | 2.62 | 24.7 | 22.1 | 74.1 | 3.5 (87) | — | 9.95 (3.32) | 9.75 (3.29) |
| 23 | xylitol | 2.4 | 15.8 | 14.1 | 47.3 | 3.8 (97) | — | 10.95 (3.65) | 10.98 (3.64) | after stirring for 30 minutes at 150° C. and distilling off the readily volatile constituents in vacuo. The product is 1,1'-O-ethylboranodiyl-bis-(2,3:5,6-di-O-ethylboranodiyl-α-D-mannofuranose).

¹H-NMR (60 Mc/s, CCl₄): τ=5.78 and 9.11 ppm in the observed ratio 13.3:25.7; calc. 14:25.

C₂₂H₃₉O₁₂B₅ (549.6) Calculated: B 9.84, Observed: B 10.02

EXAMPLE 15

2,4-O-ethylboranodiyl-β-methyl-D-xylopyranoside (XI)

A solution of 4.6 g (15.4 mmole) of BEPDIB in 10 ml of benzene is added dropwise over a period of 15 minutes at room temperature to 5 g (30.5 mmole) of β-methyl-D-xylopyranoside in 20 ml of pyridine. After stirring for 30 minutes, the mixture is concentrated in a vacuum of 10⁻³ Torr (T_max.=60° C.). Distillation in vacuo gives 5.1 g (83%) of a colourless liquid (XI) of bp. 58° C./10⁻³ Torr; $[\alpha]_D^{20}$ −113 (c=4.8, CCl₄); 0.6 g of residue. IR: 3490 cm⁻¹ (OH) Observed: B 5.4% <Calc.: B 5.35%> and observed 0.5% H⊕ <calc.: 0.5% H⊕>

EXAMPLE 24

(a) L-arabinose and D-mannose:

A solution of 18 g (60.4 mmole) of BEPDIB in 30 ml of benzene is added dropwise over a period of 30 minutes at room temperature to a stirred suspension of 4 g (26.6 mmole) of L-arabinose (mp. 136°–139° C.) and 4 g (22.2 mmole) of D-mannose in 30 ml of pyridine. The solution is concentrated in vacuo (10⁻³ Torr, bath up to 50° C.) and 7.2 g of mixture of bp. 68° C./10⁻³ Torr are distilled off. 5 g are obtained as residue.

L-arabinose:

20 ml of methanol are added to 7.2 g of distillate, followed by stirring for about 10 minutes*. All the readily volatile constituents are removed in vacuo (12 Torr). 3.8 g (95%) of colourless pure L-arabinose of mp. 156° C. are obtained as residue.

*at room temperature

D-mannose:

10 ml of ethane-1,2-diol are added to 5 g of residue, the mixture is stirred for 1 hour and all the readily volatile constituents are distilled off in vacuo (12 Torr -

$10^{-3}$ Torr). After the addition of 10 ml of ethane-1,2-diol to the viscous residue, all the readily volatile constituents are again distilled off in vacuo ($10^{-3}$ Torr). 2.9 g (73%) of D-mannose are obtained in the form of a viscous pale yellow residue. 10 ml of glacial acetic acid are added, after which crystalline product is obtained by inoculation with a D-mannose crystal.

(b) D-xylose and D-glucose:

A mixture of 5.7 g (38.4 mmole) of D-xylose of mp. 153° C. and 6.9 g (38.4 mmole) of D-glucose of mp. 143° C. is heated to approximately 80° C. with 52.7 g (176.8 mmole) of BEPDIB. The readily volatile constituents are then removed in vacuo ($10^{-3}$ Torr). Subsequent distillation gives 7.3 g of bp. 78° C./$10^{-3}$ Torr in addition to 11 g of yellowish residue.

D-xylose:

30 ml of methanol are added to 7.3 g of distillate. After heating for 10 minutes to 50° C., all the readily volatile constituents are removed in vacuo (12 to 0.1 Torr). 4.5 g (79%) of pure D-xylose of mp. 153° C. are obtained as residue.

D-glucose:

20 ml of ethane-1,2-diol are added dropwise at 50° C. to 11 g of residue and at the same time the 2-ethyl-1,3,2-dioxaborolane formed is distilled off in vacuo (10 Torr). The excess ethane-1,2-diol is removed in vacuo ($10^{-3}$ Torr, bath 80° C.). Approximately 40 ml of hexane are added to the highly viscous residue, the mixture is stirred for about 30 minutes and the white glucose is filtered off. 5 g (72%) of pure D-glucose are obtained after drying, mp. 146° C.

(c) Xylitol and D-mannitol:

A mixture of 7.46 g (41 mmole) of D-mannitol and 6.2 g (41 mmole) of xylitol is heated for 30 minutes to 80° C. with 67.5 g (227 mmole) of BEPDIB. After the readily volatile constituents have been distilled off in vacuo ($10^{-3}$ Torr), 11.6 g (96%) of bp. 108° C./$10^{-3}$ Torr and $[\alpha]_D^{20}$ 9.7 (c=6, CCl$_4$) and 9.2 g (91%) of viscous residue are obtained.

D-mannitol:

30 ml of ethane-1,2-diol are added to 11.6 g of distillate. After heating for 1 hour to 60° C., all the volatile constituents are removed in vacuo ($10^{-3}$ Torr). 5.8 g (78%) of pure D-mannitol of mp. 164°–166° C. are obtained as residue.

Xylitol:

9.2 g of residue are heated for 30 minutes to 60° C. in 30 ml of ethane-1,2-diol. The volatile constituents are removed in vacuo ($10^{-3}$ Torr). 4 g (65%) of pure xylitol of mp. 90° C. are obtained as residue.

EXAMPLES 25–35

The general procedure of Example 2 was followed using ethylboroxin instead of BEPDIB and using toluene as reaction medium instead of benzene and/or pyridin (Table 7). The temperature was raised after mixing up to 110° C. at which temperature the reaction water was distilled off as an aceotropic mixture with toluene. The Roman numbers of products I–VIII, X, XII, XIII, and XXVII correspond to the products identified on pages 9–11 of the disclosure, whereas XXII corresponds to the product of Example 14 on page 17. In Example 34 besides product No. XII a further new compound XXIII is formed:

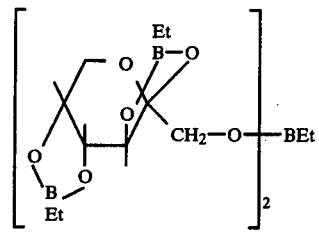

This compound is 1,1'-O-ethylboranodiyl-bis-(2,3:4,5-di-O-ethylboranodiyl-β-D-fructopyranose having a molecular weight (NMR)=550 (B$_5$) containing B=9.63%, B$_c$=3.3%.

According to Example 29 besides product No. V a new compound XXIV, 4,5-O-ethylboranodiyl-2,3-didesoxy-D-glycero-pent-2-enose, is formed with a yield of 3.36% having BP=55° C./$10^{-3}$ Torr, $[\alpha]_D^{20}=17.1$ (c=1.7 CCl$_4$), molecular weight (NMR)=154 (B$_1$).

The general procedure of Examples 25–35 may be illustrated once more by describing Example 29:

The suspension of 18.9 g (141 mmol) 2-desoxy-D-ribose in 60 ml toluene together with 7.9 g (47 mmol) ethylboroxin was heated to 110° C. under stirring. The water/toluene-aceotrop was distilled off. Thereafter, 2.4 g of pure 4,5-O-ethylboranediyl-4,5-dihydroxypent-3-enal were distilled in vacuum at a BP of 55° C./$10^{-3}$ Torr (yield 22%) as well as 11.9 g of a mixture ($^1$H-NMR: about 50% pent-3-enal-derivative and 50% V). There was a dark brown residue of 3.4 g.

EXAMPLE 36

Separation of D-xylose from xylit 10 g (66.6 mmol) D-xylose and 10 g (65.7 mmol) xylit were mixed in 90 ml benzene and thereafter 23.3 g (138.7 mmol) ethylboroxin were added. After quantitative removal of the water/benzene-aceotrop vacuum distillation resulted in 16.4 g of III, BP 74° C./$10^{-3}$ Torr (yield 96%). 16.6 g residue contained the O-ethyl-borandiyl-derivative of the xylit. To isolate the pure D-xylose out of III 200 ml methanol were dropped to the vacuum distillate and the light volatile part currently distilled off. 9.2 g of colourless, solid D-xylose of a melting point at 142° C. were isolated (95.8% yield). The residue was mixed with 40 ml of a 1:1 mixture of ethylene-glycole/ethanol and the mixture distilled in high vacuum. The residue 10.2 g is raw xylit (yield 102%).

Table 7

| | | | Production of O-Ethylborandiyl-sugar with Ethylboroxin | | | | |
|---|---|---|---|---|---|---|---|
| Example | Poly-hydroxy-compound | g (mmol) | Ethyl-boroxin g (mmol) | Product No. | g (mmol) | Yield % | B.P.(°C./Torr.) |
| 25 | D-Ribose | 30.8 (205.2) | 27.8 (165.9) | I | 44.4 | 95.8 | 78/$10^{-3}$ |
| | | 10.2 | 14.3 | I | 14.8 | 96.7 | 85/5 . $10^{-3}$ |

Table 7-continued

| | | Production of O-Ethylborandiyl-sugar with Ethylboroxin | | | | | |
|---|---|---|---|---|---|---|---|
| Example | Poly-hydroxy-compound | g (mmol) | Ethyl-boroxin g (mmol) | Product No. | g (mmol) | Yield % | B.P.(°C./Torr.) |
| 26 | L-Arabinose | (68.0) 3.0 (20.0) | (85.1) 3.4 (20.0) | II | 4.4 | 97.8 | 68–69/10$^{-3}$ |
| 27 | D-Xylose | 20.0 (95.2) | 16 (95.2) | III | 27 | 90 | 74/10$^{-3}$ |
| 28 | L-Rhamnose | 4.1 (24.9) | 5.3 (31.5) | IV | 5.4 | 91.5 | 77–78/10$^{-3}$ |
| | | 20.8 (126.7) | 7.1 (42.3) | XVII | 24.4 | 95 | — |
| 29 | 2-Desoxy-D-ribose | 18.9 (141) | 7.9 (47) | V | | 18 | 95/10$^{-3}$ |
| 30 | D-Mannose | 97.7 (542.5) | 60.8 (361.9) | α/β-VI | 101.7 | 74 | 126/10$^{-3}$ |
| | | 31.8 (176.5) | 19.8 (117.6) | α/β-VI 9:1 | 37.2 | 82.5 | 126/10$^{-3}$ |
| | | 13.5 (74.9) | 50.3 (299.6) | XXII | 20.5 | 99.6 | — |
| 31 | D-Glucose | 37.1 (205.1) | 23.1 (137.5) | VII | 44.8 | 85 | 120/10$^{-3}$ |
| 32 | Galactose | 18 (100) | 11.2 (66.6) | VIII | 21.8 | 85.5 | 119/10$^{-3}$ |
| 33 | Methyl-D-glucopyranosid | 20 (103.1) | 5.8 (34.4) | X | 20.2 | 84.5 | 140/10$^{-3}$ |
| 34 | D-Fructose | 100 (555.2) | 62.2 (370.2) | XII | 128 | 90.2 | 99/10$^{-3}$ |
| | | 28.3 (110.6) | 5.8 (34.5) | XXIII | 30.3 | 99.7 | -viscos |
| 35 | L-Sorbose | 100 (555.1) | 64.9 (386.3) | XIII | 128 | 90.2 | 120/10$^{-3}$ |

We claim:

1. A process for the separation and purification of an oligo or polyhydroxy compound by introducing and subsequently eliminating protective groups, wherein the oligo and polyhydroxy compound is contacted with bis-(ethylpivaloyloxy)-diboroxane, or ethylboroxin, for formation of the O-ethylboranodiyl derivative of the hydroxy compound and the O-ethylboranodiyl derivative is separated and the O-ethylboranodiyl protective groups are eliminated by an alcoholic compound for deborylation of the O-ethylboranodiyl derivative.

2. Process of claim 1, wherein the oligo or polyhydroxy compound is contacted with bis-(ethylpivaloyloxy)-diboroxane.

3. Process of claim 1, wherein the oligo or polyhydroxy compound is contacted with ethylboroxin.

4. Process of claim 1, wherein said separation is by distilling under vacuum.

5. Process of claim 1, wherein said reaction is performed at about −10° C. to about +150° C.

6. Process of claim 1, wherein said reaction is carried out in the absence of water.

7. Process of claim 1, wherein said reaction is carried out in the presence of an inert gas.

8. Process of claim 1, wherein said alcoholic compound is methanol or glycol.

9. Process of claim 1, wherein said separation is by distilling under vacuum, said reaction is performed at about −10° C. to about +150° C., said reaction is carried out in the absence of water, said reaction is carried out in the presence of an inert gas, and said alcoholic compound is methanol or glycol.

10. Process of claim 1, wherein the oligo or polyhydroxy compound has sterically attachable hydroxy groups for the formation of O-ethylboranodiyl derivative.

11. Process of claim 1, wherein the oligo or polyhydroxy compound is an alkane polyol, aldo- or keto- tri- to heptaoses, saccharides, desoxy sugars, sugar carboxylic acids and their anhydrides and polymers containing hydroxy groups.

12. Compounds of the group:
1,2:3,4-bis-O-ethylboranodiyl-α-D-ribopyranose
1,2:3,4-bis-O-ethylboranodiyl-β-L-arabinopyranose
1,2:3,5-bis-O-ethylboranodiyl-α-D-xylorfuranose
1,2:3,5-bis-O-ethylboranodiyl-β-L-rhamnopyranose
3,4-O-ethylboranodiyl-2-desoxy-β-D-ribopyranose
  with a free OH-group in the 1-position
2,3:5,6-bis-ethylboranodiyl-α-D-mannofuranose with a free OH-group in the 1-position
1,2:3,5-bis-O-ethylboranodiyl-α-D-glucofuranose with a free OH-group in the 6-position
1,2:3,4-bis-O-ethylboranodiyl-α-D-galactopyranose with a free OH-group in the 6-position
2,3:4,6-bis-O-ethylboranodiyl-α-methyl-D-mannopyranoside
4,6-O-ethylboranodiyl-α-methyl-D-glucopyranoside with free OH-groups in the 2- and 3-positions
2,4-O-ethylboranodiyl-β-methyl-D-xylopyranoside with a free OH-group in the 3-position
2,3:4,5-bis-O-ethylboranodiyl-β-D-fructopyranose with a free OH-group in the 1-position
2,3:4,6-bis-O-ethylboranodiyl-α-L-sorbofuranose with a free OH-group in the 1-position
1,2:3,4-bis-O-ethylboranodiyl-D-tagatofuranose with a free OH-group in the 2-position
3,4-O-ethylboranodiyl-methyl-L-parabinopyranoside with a free OH-group in the 2-position
2,3-O-ethylboranodiyl-β-D-ribopyranoside with free OH-groups in the 1- and 4-positions 2,3-O-ethylboranodiyl-α-rhamnofuranose with free OH-groups in the 1- and 5-positions 2,3-O-ethylboranodiyl-D-ribopentono-1,4-lactone with a free OH-group in the 5-position 1,2-O-ethylboranodiyl-D-glucurono-3,6-lactone with a free OH-group in the 5-position 4,6-O-ethylboranodiyl-N-acetyl-D-glucosamine with free OH-groups in the 1- and 3-positions 6,6'-O-ethylboranodiyl-bis-(1,2:3,5-di-O-ethylboranodiyl-α-D-glucofuranose)

1,1'-O-ethylboranodiyl-bis-(2,3:5,6-di-O-ethylboranodiyl-α-D-mannofuranose)

1,1'-O-ethylboranodiyl-bis-(2,3:4,5-di-O-ethylboranodiyl-β-D-fructopyranose)

4,5-O-ethylboranodiyl-2,3-didesoxy-D-glycero-pent-2-enose.

13. Compound of claim 12, which is 1,2:3,4-bis-O-ethylboranodiyl-α-D-ribopyranose.

14. Compound of claim 12, which is 1,2:3,4-bis-O-ethylboranodiyl-β-L-arabinopyranose.

15. Compound of claim 12, which is 1,2:3,5-bis-O-ethylboranodiyl-α-D-xylorfuranose.

16. Compound of claim 12, which is 1,2:3,5-bis-O-ethylboranodiyl-β-L-rhamnopyranose.

17. Compound of claim 12, which is 3,4-O-ethylboranodiyl-2-desoxy-β-D-ribopyranose with a free OH-group in the 1-position.

18. Compound of claim 12, which is 2,3:5,6-bis-ethylboranodiyl-α-D-mannofuranose with a free OH-group in the 1-position.

19. Compound of claim 12, which is 1,2:3,5-bis-O-ethylboranodiyl-α-D-glucofuranose with a free OH-group in the 6-position.

20. Compound of claim 12, which is 1,2:3,4-bis-O-ethylboranodiyl-α-D-galactopyranose with a free OH-group in the 6-position.

21. Compound of claim 12, which is 2,3:4,6-bis-O-ethylboranodiyl-α-methyl-D-mannopyranoside.

22. Compound of claim 12, which is 4,6-O-ethylboranodiyl-α-methyl-D-glucopyranoside with free OH-groups in the 2- and 3-position.

23. Compound of claim 12, which is 2,4-O-ethylboranodiyl-β-methyl-D-xylopyranoside with a free OH-group in the 3-position.

24. Compound of claim 12, which is 2,3:4,5-bis-O-ethylboranodiyl-β-D-fructopyranose with a free OH-group in the 1-position.

25. Compound of claim 12, which is 2,3:4,6-bis-O-ethylboranodiyl-α-L-sorbofuranose with a free OH-group in the 1-position.

26. Compound of claim 12, which is 1,2:3,4-bis-O-ethylboranodiyl-D-tagatofuranose with a free OH-group in the 2-position.

27. Compound of claim 12, which is 3,4-O-ethylboranodiyl-methyl-L-parabinopyranoside with a free OH-group in the 2-position.

28. Compound of claim 12, which is 2,3-O-ethylboranodiyl-β-D-ribopyranoside with free OH-groups in the 1- and 4-position.

29. Compound of claim 12, which is 2,3-O-ethylboranodiyl-α-rhamnofuranose with free OH-groups in the 1- and 5-position.

30. Compound of claim 12, which is 2,3-O-ethylboranodiyl-D-ribopentono-1,4-lactone with a free OH-group in the 5-position.

31. Compound of claim 12, which is 1,2-O-ethylboranodiyl-D-glucurono-3,6-lactone with a free OH-group in the 5-position.

32. Compound of claim 12, which is 4,6-O-ethylboranodiyl-N-acetyl-D-glucosamine with free OH-groups in the 1- and 3-position.

33. Compound of claim 12 which is 6,6'-O-ethylboranodiyl-bis-(1,2:3,5-di-O-ethylboranodiyl-α-D-glucofuranose).

34. Compound of claim 12 which is 1,1'-O-ethylboranodiyl-bis-(2,3:5,6-di-O-ethylboranodiyl-α-D-mannofuranose).

35. Compound of claim 12 which is 1,1'-O-ethylboranodiyl-bis-(2,3:4,5-di-O-ethylboranodiyl-β-D-fructopyranose).

36. Compound of claim 12 which is 4,5-O-ethylboranodiyl-2,3-didesoxy-D-glycero-pent-2-enose.

* * * * *